(12) United States Patent
Motisi et al.

(10) Patent No.: US 6,544,235 B2
(45) Date of Patent: Apr. 8, 2003

(54) VALVE FOR USE WITH A CATHETER

(76) Inventors: Steven A. Motisi, 44W738 Littlewoods Trail, Hampshire, IL (US) 60140; Thomas C. Bumsted, 38W643 Bittersweet La., Elgin, IL (US) 60123; Paul J. Motisi, 6129 N. Navarre, Chicago, IL (US) 60631

( * ) Notice: Subject to any disclaimer, the term of this patent is extended or adjusted under 35 U.S.C. 154(b) by 92 days.

(21) Appl. No.: 09/848,645

(22) Filed: May 3, 2001

(65) Prior Publication Data

US 2002/0165502 A1 Nov. 7, 2002

(51) Int. Cl.$^7$ ................................................ A61M 5/00
(52) U.S. Cl. ....................................... 604/249; 604/247
(58) Field of Search .............................. 604/247, 249, 604/250, 93.01, 9, 256, 30, 31, 34, 167.03, 167.04, 167.05, 236, 237, 288.03, 323

(56) References Cited

U.S. PATENT DOCUMENTS

| | | |
|---|---|---|
| 3,601,152 A | 8/1971 | Kenworthy |
| 3,610,226 A | 10/1971 | Albisser |
| 3,889,710 A | 6/1975 | Brost |
| 3,997,923 A | 12/1976 | Possis |
| 4,005,710 A | 2/1977 | Zeddies et al. |
| 4,141,379 A | 2/1979 | Manske |
| 4,143,853 A | 3/1979 | Abramson |
| 4,244,378 A | 1/1981 | Brignola |
| 4,286,628 A | 9/1981 | Paradis et al. |
| 4,310,017 A | 1/1982 | Raines |
| 4,468,224 A * | 8/1984 | Enzmann et al. ........... 604/247 |
| 4,660,569 A | 4/1987 | Etherington |
| 4,666,429 A * | 5/1987 | Stone .......................... 604/83 |
| 4,784,156 A | 11/1988 | Garg |
| 4,813,941 A | 3/1989 | Shea |
| 4,832,044 A | 5/1989 | Garg |
| 4,840,184 A | 6/1989 | Garg |
| 4,844,087 A | 7/1989 | Garg |
| 4,865,587 A | 9/1989 | Walling |
| 5,045,065 A | 9/1991 | Raulerson |
| 5,487,734 A | 1/1996 | Thorne et al. |
| 5,727,594 A * | 3/1998 | Choksi ........................ 137/859 |
| 5,735,826 A * | 4/1998 | Richmond ................... 604/251 |
| 5,843,046 A | 12/1998 | Motisi et al. |
| 5,941,499 A | 8/1999 | Wollschlager |
| 5,961,472 A | 10/1999 | Swendson et al. |
| 6,149,632 A | 11/2000 | Landuyt |
| 6,158,467 A | 12/2000 | Loo |

* cited by examiner

Primary Examiner—Manuel Mendez
(74) Attorney, Agent, or Firm—Mathew R. P. Perrone, Jr.

(57) ABSTRACT

A valve, insertable in a standard catheter, prevents undesired backflow of fluid and provides for blood samples to be taken through a standard catheter. This valve is a check valve having a housing with a check plate mounted therein.

12 Claims, 3 Drawing Sheets

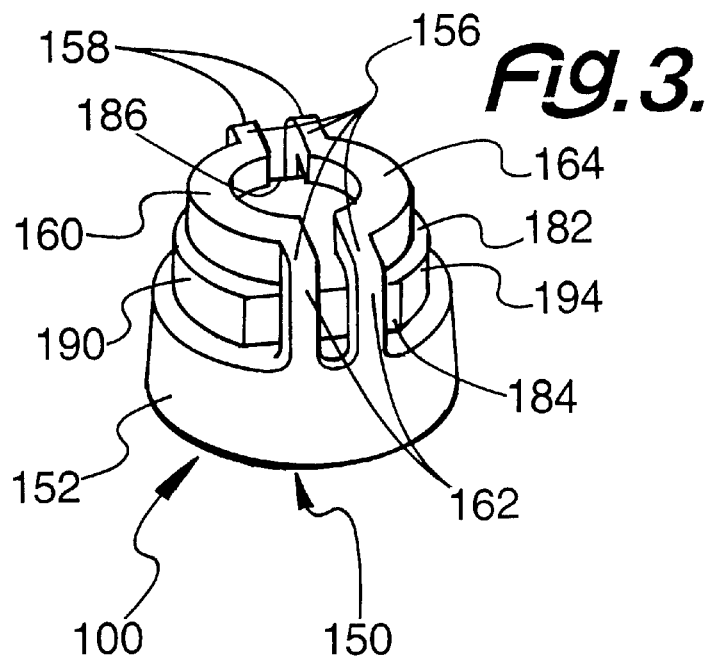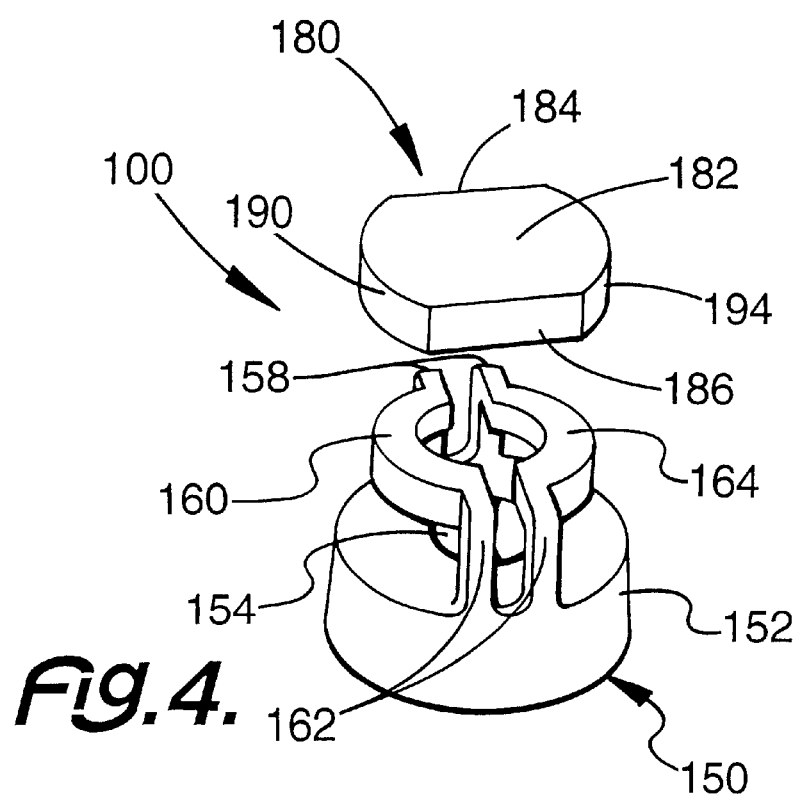

VALVE FOR USE WITH A CATHETER

This invention relates to a catheter and, more particularly to a valve for use with a standard catheter, which minimizes back flow of fluid.

BACKGROUND OF THE INVENTION

In modern medicine, a catheter has many uses. A catheter for intravenous use has a flexible tube of various lengths attached to a hub. A needle assembly cooperates with the catheter, in order for the flexible tube to be inserted into a patient. After the needle is removed, then appropriate medication or other desired material is inserted through the hub into the flexible tube and thence into the patient.

In operation, the catheter is inserted into a patient with the needle assembly. A needle of the needle assembly is inserted into a blood vessel of a person. The tube from the catheter is pushed down the needle, threaded therethrough, thereby inserting the tube and leaving the same in that blood vessel. Attached to the hub of the catheter may be a series of devices, which permit access to the tube. In this manner, a person may be given medicine, have blood samples drawn therefrom, or receive any other desirable medical procedure requiring fluid to be put in or taken out as desired.

Undesired fluid flow is a problem with the catheter. Many types of check valves are known for preventing such an undesired fluid flow. Typically, adding a check valve requires replacement of the entire catheter unit. Most hospitals are reluctant to take such action and do a complete replacement of familiar equipment. If a check valve can be developed and used with an existing catheter, great advantages are obtained.

Some of those check valves save an elastomeric nature, which causes a sealing of the valve and stoppage of the fluid flow as undesired pressure is put on the check valves. Unfortunately, these elastormeric valves are expensive. Furthermore, such valves need to be replaced often because they lack durability.

Sometimes an elastomeric valve is used with a concave seam surface. Such a valve must be a floating valve and smaller than the concave area. Such a structure permits debris to be trapped between the valve disc and the concave surface. Such debris, of course, interferes with the proper functioning of the catheter.

Another desired use of a catheter is to permit blood samples to be taken therethrough. However, a check valve can interfere with this procedure. Thus, the check valves of the prior art cause other problems, too.

A check valve must work in the catheter. Flow of fluid interference must be minimized. Also, there must be no interference with a desired fluid flow. Such required features are clearly contrary. Maximizing of one feature minimizes the ability to maximize the advantage of the other feature. Thus, a check valve which can maximize the advantages of both requirements provides a great advantage to the art.

SUMMARY OF THE INVENTION

Therefore, among the many objectives of this invention is to provide a valve, which is insertable into an existing catheter.

A further objective of this invention is to provide a check valve for a catheter.

A still further objective of this invention is to provide a valve for a catheter, which permits drawing of blood samples through the catheter.

Yet a further objective of this invention is to provide a valve for a catheter, which minimizes undesired pressure on the valve.

Also, an objective of this invention is to provide a durable check valve for a catheter.

Another objective of this invention is to provide a valve for a catheter, which minimizes undesired fluid flow.

Yet another objective of this invention is to provide a valve for a catheter having a simply designed structure.

Still, another objective of this invention is to provide a valve for a catheter being easily manufactured.

These and other objectives of the invention (which other objectives become clear by consideration of the specification, claims and drawings as a whole) are met by providing a valve insertable in a standard catheter, wherein the valve prevents undesired backflow of fluid and provides for blood samples to be taken through a standard catheter.

BRIEF DESCRIPTION OF THE DRAWINGS

FIG. 3 depicts a perspective view of the valve 100 of this invention.

FIG. 4 depicts an exploded, perspective view of the valve 100 of this invention.

FIG. 5 depicts a rear plan view of the valve 100 of this invention in open position 130, a reverse view thereof being substantially similar.

FIG. 6 depicts a rear plan view of the valve 100 of this invention in closed position 140, a reverse view thereof being substantially similar.

Throughout the figures of the drawings, where the same part appears in more than one figure of the drawings, the same number is applied thereto.

DESCRIPTION OF THE PREFERRED EMBODIMENTS

Into a catheter is inserted a check valve. The check valve includes a housing and a check plate. The housing has a valve body with a support device and as an integral part thereof. Centrally located in the valve body is a fluid aperture. The valve body itself is perfectly cylindrical in appearance.

The support device includes struts extending upwardly from the valve body. There are four struts. Connected to the four struts is the plate stop. The plate stop includes a pair of arcuate members connected to a pair of struts. Each arcuate member interconnects two ends of the four struts at each end of the arc.

The plate stop is generally cylindrical in shape. However, a top view of the plate stop depicts a circle with two parallel cords removed therefrom. More specifically, the plate stop is a cylinder with two parallel flattened sides. Thus, the plate stop may slide under each arcuate member and between a pair of struts. The struts have sufficient length in order to permit the plate stop to move back and forth between the valve body and the arcuate members, thereby providing an opening and closing of the check valve. The shape of the catheter prevents or substantially eliminates other movements of the plate stop within the valve body, except for the back and forth movement.

Such a structure permits the valve to be inserted into a standard catheter. The assembly greatly restricts, if not eliminates, undesired backflow. Between the plate and a top portion of the valve body, a tight seal is permitted. Due to the structure and materials used, little or no leakage occurs around the valve.

Figure 1:
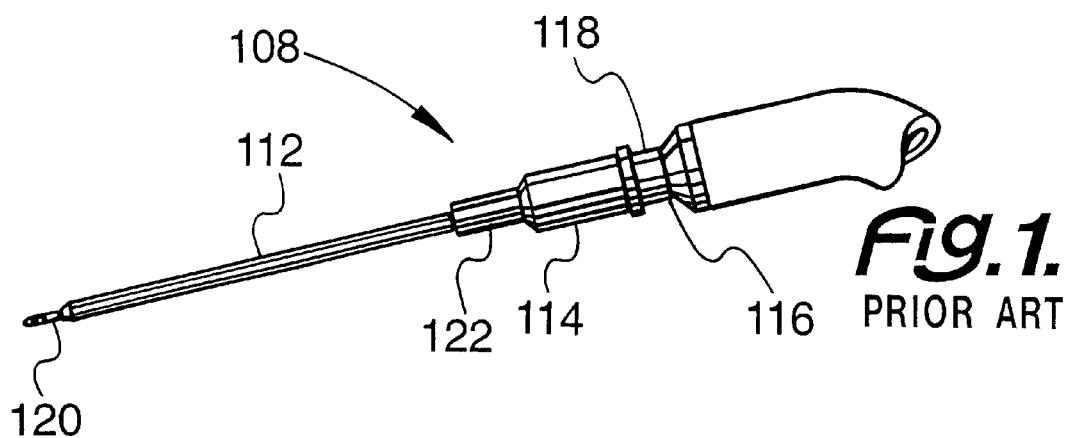
FIG. 1 depicts a perspective view of a prior art catheter 108.

Referring now to FIG. 1, catheter 108 is depicted as having a tube 112 extending from a hub 114. Through the hub 114 and the tube 112 fits needle assembly 116. Needle assembly 116 has a needle housing 118 with a needle 120 extending through tube 112. As needle 120 is inserted into a patient (not shown) tube 112 is moved into the opening created by needle 120. As needle housing 118, and therefore needle 120, is removed from catheter 108, tube 112 is left in the patient. Various desired medicines or other material can then be given to the patient through catheter 108, by forcing the same through hub 114 into tube 112.

Figure 2:
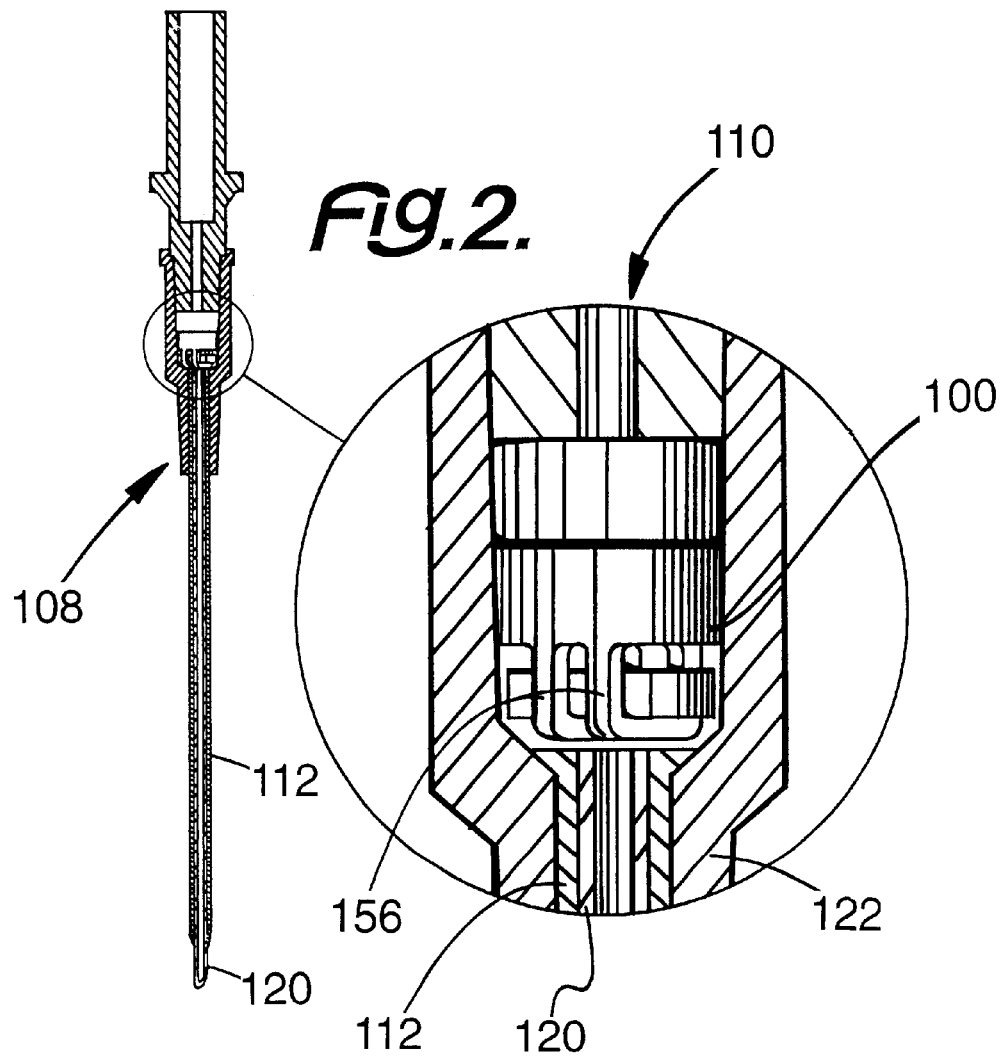
FIG. 2 depicts a side, cross-sectioned view of catheter 108, with a magnified section 112 showing the valve 100 of this invention in position within a magnified section 110 of catheter 108.

At the juncture of the hub 114 and the tube 112 is a step 122. The check valve 100 of this invention, as shown in position within magnified section 110 of FIG. 2, fits into catheter 100 at step 122. Check valve 100 renders catheter 108 more efficient in that backflow from the patient through tube 112 is substantially avoided, while still permitting blood to be drawn through catheter 108.

Adding FIG. 3 and FIG. 4 to the consideration, this check valve 100 includes a housing 150 with a check plate 180 inserted therein. Housing 150 includes a valve body 152 with a fluid aperture 154 centrally located therein. Extending from the valve body 152 are four struts 156 generally forming the corners of a rectangle. A first pair 158 of the four struts 156 is connected by a first plate stop 160. A second pair 162 of the four struts 156 is connected by a second plate stop 164.

The four struts 156 are positioned in the catheter 108 adjacent to the tube 112. Within the four struts 156 is positioned check plate 180. Check plate 180 appears to be a circular disk 182 with two parallel cords removed therefrom in order to form first parallel side 184 and second parallel side 186.

Preferably first plate stop 160 and second plate stop 164 are substantially symmetrical to each other. A more preferred structure requires that both first plate stop 160 and second plate stop 164 be generally arcuate in shape, mutually coplanar, and parallel to valve body 160. Check plate 180 fits between valve body 160, and first plate stop 160 and second plate stop 164. Check plate 180 closes aperture 132 if desired.

Clearly, with first parallel side 182 and parallel side 184, check plate 180 has a first arcuate end 190 opposing second arcuate end 194. First arcuate end 190 is adjacent to first plate stop 160, while second arcuate end 194 is adjacent to second plate stop 194. Check plate 180 moves between struts 156 and valve body 160, and preferably and standardly reciprocally or back forth, but not side to side.

Figure 5:
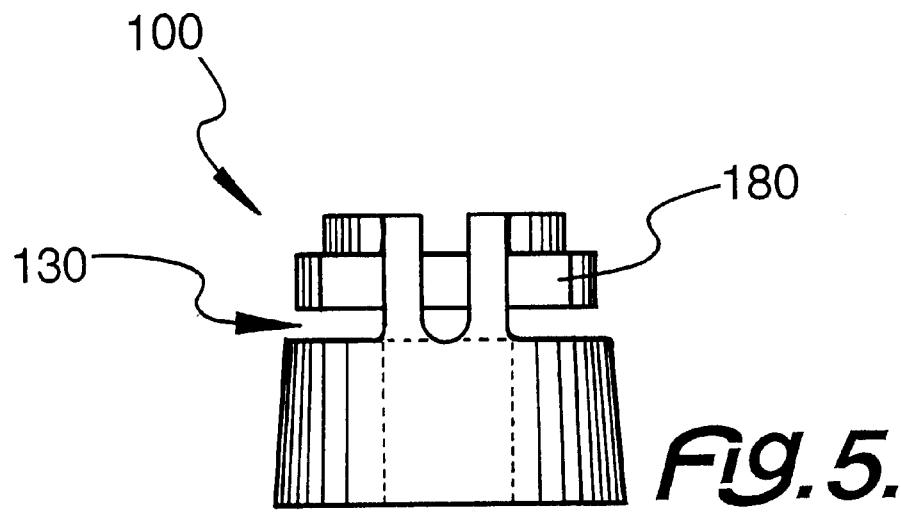
Figure 6:
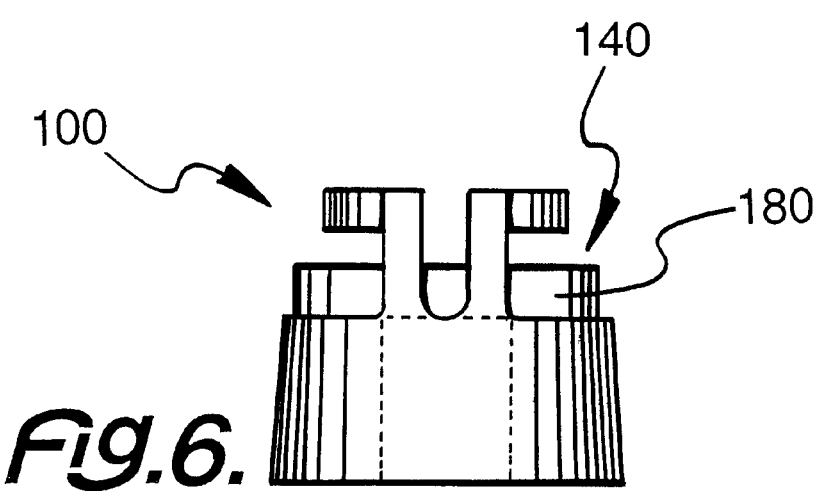

Further adding FIG. 5 and FIG. 6 to the consideration, housing 150 with a check plate 180 has open position 130 (FIG. 5) differing from closed position 140 (FIG. 6). Closed position 130 has check plate 180 adjacent to valve body 160. Open position 140 has check plate 180 spaced from valve body 160, but restrained by the cooperation of first plate stop 160 and second plate stop 164. Open position 140 permits fluid passage through check valve 100, and catheter 108, while closed position 130 greatly restricts or even eliminates fluid passage through check valve 100, and catheter 108.

This application—taken as a whole with the specification, claims, abstract, and drawings—provides sufficient information for a person having ordinary skill in the art to practice the invention disclosed and claimed herein. Any measures necessary to practice this invention are well within the skill of a person having ordinary skill in this art after that person has made a careful study of this disclosure.

Because of this disclosure and solely because of this disclosure, modification of this method and apparatus can become clear to a person having ordinary skill in this particular art. Such modifications are clearly covered by this disclosure.

What is claimed and sought to be protected by Letters Patent of the United States is:

1. A check valve adapted for insertion into a standard catheter comprising:
    (a) a housing for the valve being adapted to fit in a standard catheter;
    (b) a check plate being receivable in the housing to complete the valve;
    (c) the check plate being movable within the housing in order to open and close the valve;
    (d) the check plate being reciprocally movable within the housing;
    (e) the housing having a valve body and a support device;
    (f) the valve body including a fluid aperture;
    (g) the support device extending from the valve body;
    (h) the support device cooperating with the valve body in order to receive the check plate;
    (i) the support device extending from the valve body;
    (j) the support device including a strut assembly;
    (k) the strut assembly extending upwardly from the valve body;
    (l) a plate stop being joined to the strut assembly;
    (m) the strut assembly including four struts;
    (n) the four struts extending upwardly from the valve body;
    (o) the plate stop having a first arcuate member and a second arcuate member;
    (p) the four struts having a first pair of struts and a second pair of struts;
    (q) the plate stop having a first arcuate member and a second arcuate member;
    (r) the four struts including a first pair of struts and a second pair of struts;
    (s) the first arcuate member connecting the first pair of struts; and
    (t) the second arcuate member connecting the second pair of struts.

2. The check valve of claim 1 further comprising:
    (a) the plate stop having a generally cylindrical shape;
    (b) the plate stop having a pair of parallel flat sides;
    (c) each member of the pair of parallel flat sides contacting a pair of the four struts; and
    (d) the plate stop having a thickness sufficient to permit movement of the plate stop between the arcuate members and the valve body.

3. The check valve of claim 2 further comprising:
    (a) the housing with the plate stop being adapted to fit into a catheter; and
    (b) the housing with the catheter cooperating to hold the plate stop in position.

4. In a catheter having a tube extending from a hub wherein the tube fits into a needle assembly and a juncture is situated between the hub and the tube, the improvement comprising:

(a) a check valve being into adapted for the juncture; a standard catheter comprising:
(b) a housing for the valve being adapted to fit in a standard catheter;
(c) a check plate being receivable in the housing to complete the valve;
(d) the check plate being movable within the housing in order to open and close the valve;
(e) the check plate being reciprocally movable within the housing;
(f) the housing having a valve body and a support device;
(g) the valve body including a fluid aperture;
(h) the support device extending from the valve body;
(i) the support device cooperating with the valve body in order to receive the check plate;
(j) the support device extending from the valve body;
(k) the support device including a strut assembly;
(l) the strut assembly extending upwardly from the valve body;
(m) a plate stop being joined to the strut assembly;
(n) the strut assembly including four struts;
(o) the four struts extending upwardly from the valve body;
(p) the plate stop having a first arcuate member and a second arcuate member;
(q) the four struts having a first pair of struts and a second pair of struts;
(r) the plate stop having a first arcuate member and a second arcuate member;
(s) the four struts including a first pair of struts and a second pair of struts;
(t) the first arcuate member connecting the first pair of struts; and
(u) the second arcuate member connecting the second pair of struts.

5. The catheter of claim 4 further comprising:
(a) the plate stop having a generally cylindrical shape;
(b) the plate stop having a pair of parallel flat sides;
(c) each member of the pair of parallel flat sides contacting a pair of the four struts; and
(d) the plate stop having a thickness sufficient to permit movement of the plate stop between the arcuate members and the valve body.

6. The catheter of claim 5 further comprising:
(a) the housing with the plate stop being adapted to fit into a catheter; and
(b) the housing with the catheter cooperating to hold the plate stop in position.

7. A check valve adapted for insertion into a standard catheter comprising:
(a) a housing for the valve being adapted to fit in a standard catheter;
(b) a check plate being receivable in the housing to complete the valve;
(c) the check plate being movable within the housing in order to open and close the valve;
(d) the check plate being reciprocally movable within the housing;
(e) the housing having a valve body and a support device;
(f) the valve body including a fluid aperture;
(g) the support device extending from the valve body;
(h) the check plate having limited movement within the support device;
(i) the support device cooperating with the valve body in order to receive the check plate;
(j) the support device extending from the valve body;
(k) the support device including a strut assembly;
(l) the strut assembly extending upwardly from the valve body;
(m) a plate stop being joined to the strut assembly;
(n) the strut assembly including four struts;
(o) the four struts extending upwardly from the valve body;
(p) the plate stop having a first arcuate member and a second arcuate member;
(q) the four struts having a first pair off struts and a second pair of struts;
(r) the plate stop having a first arcuate member and a second arcuate member;
(s) the four struts including a first pair of struts and a second pair of struts;
(t) the first arcuate member connecting the first pair of struts; and
(u) the second arcuate member connecting the second pair of struts.

8. The check valve of claim 7 further comprising:
(a) the plate stop having a generally cylindrical shape;
(b) the plate stop having a pair of parallel flat sides;
(c) each member of the pair of parallel flat sides contacting a pair of the four struts; and
(d) the plate stop having a thickness sufficient to permit movement of the plate stop between the arcuate members and the valve body.

9. The check valve of claim 8 further comprising:
(a) the housing with the plate stop being adapted to fit into a catheter; and
(b) the housing with the catheter cooperating to hold the plate stop in position.

10. The check valve of claim 9 further comprising:
(a) the catheter having a tube extending from a hub wherein the tube fits into a needle assembly and a juncture is situated between the hub and the tube;
(b) the check valve being adapted to fit into the juncture;
(c) a housing for the valve being adapted to fit in a standard catheter;
(d) a check plate being receivable in the housing to complete the valve;
(e) a check plate being receivable in the housing to complete the valve;
(e) the check plate being movable within the housing in order to open and close the valve; and
(f) the check plate being reciprocally movable within the housing.

11. The check valve of claim 10 further comprising:
(a) the housing having a valve body and a support device;
(b) the valve body including a fluid aperture;
(c) the support device extending from the valve body; and
(d) the support device cooperating with the valve body in order to receive the check plate.

12. The check valve of claim 11 further comprising:
(a) the support device extending from the valve body;
(b) the support device including a strut assembly;

(c) the strut assembly extending upwardly from the valve body;
(d) a plate stop being joined to the strut assembly.
(e) the strut assembly including four struts;
(f) the four struts extending upwardly from the valve body;
(g) the plate stop having a first arcuate member and a second arcuate member;
(h) the four struts having a first pair of struts and a second pair of struts;
(i) the plate stop having a first arcuate member and a second arcuate member;
(j) the four struts including a first pair of struts and a second pair of struts;
(k) the first arcuate member connecting the first pair of struts; and
(l) the second arcuate member connecting the second pair of struts.

* * * * *